United States Patent [19]

Iwasaki et al.

[11] Patent Number: 4,821,738
[45] Date of Patent: Apr. 18, 1989

[54] ARTERIAL BLOOD GAS SYRINGE
[75] Inventors: Dean H. Iwasaki, Denver; Michael D. Iliff, Conifer, both of Colo.
[73] Assignee: Marquest Medical Products, Inc., Englewood, Colo.
[21] Appl. No.: 122,892
[22] Filed: Nov. 19, 1987
[51] Int. Cl.⁴ ............................................... A61B 5/00
[52] U.S. Cl. ..................................... 128/765; 604/190
[58] Field of Search ....................... 604/190, 187, 222; 128/765, 766, 767

[56] References Cited
U.S. PATENT DOCUMENTS
4,424,817 1/1984 Williams .
4,448,206 5/1984 Martell ................................. 128/765
4,466,446 8/1984 Baidwan et al. .
4,690,154 9/1987 Woodford et al. .
4,703,763 11/1987 McAlister et al. ................... 128/765

Primary Examiner—John D. Yasko
Attorney, Agent, or Firm—Sheridan, Ross & McIntosh

[57] ABSTRACT

An arterial blood gas syringe is disclosed for obtaining an arterial blood sample. The syringe is characterized by a sealing plug having channels formed in an upper surface thereof for use in removing air as arterial blood is received into the syringe. Each of the channels extends in a generally radial direction and the channels converge near the center of the sealing plug. A filter element is contained in the center of the sealing plug for permitting the passage of air directed thereto using the channels. The filter element permits the passage of the air but prevents passage of the blood.

10 Claims, 2 Drawing Sheets

U.S. Patent  Apr. 18, 1989  Sheet 1 of 2  4,821,738
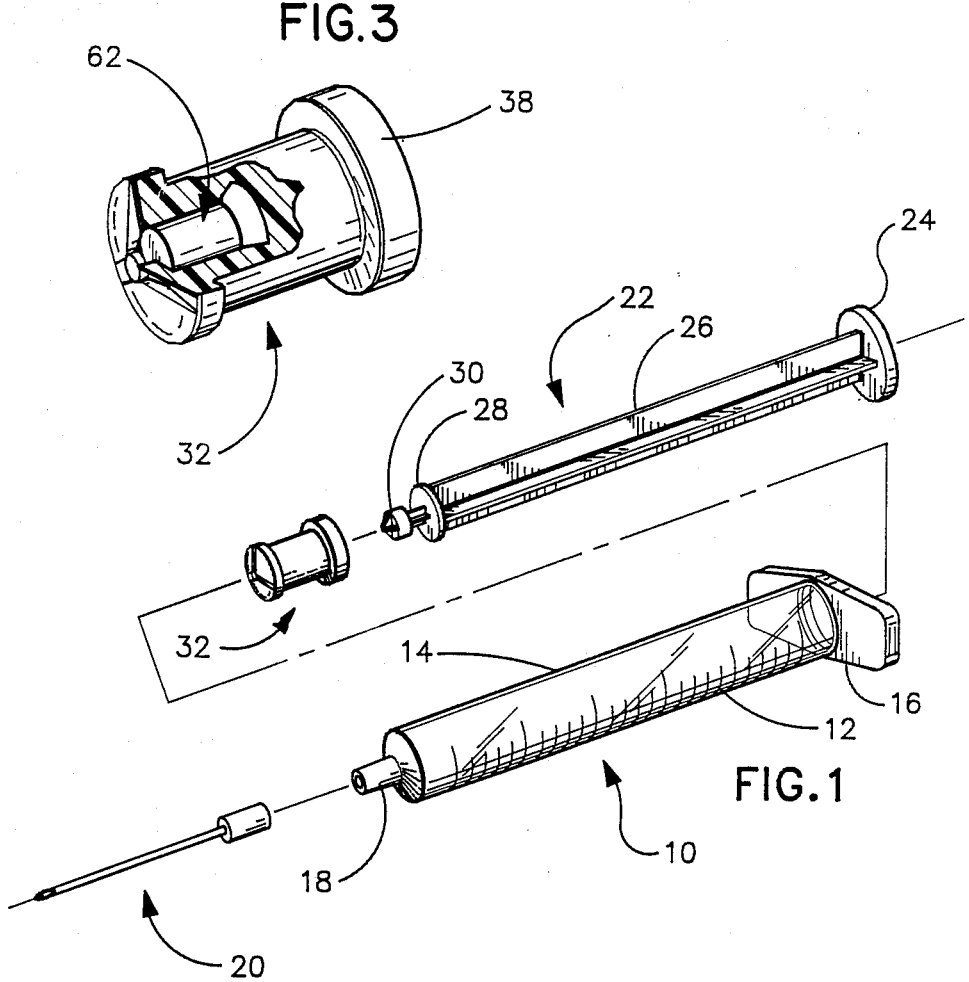
FIG. 3
FIG. 1
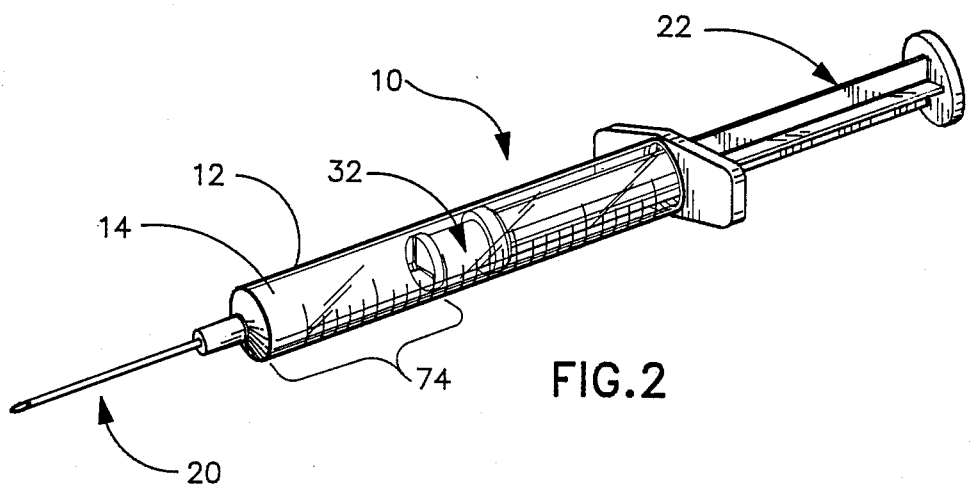
FIG. 2

U.S. Patent   Apr. 18, 1989   Sheet 2 of 2   4,821,738
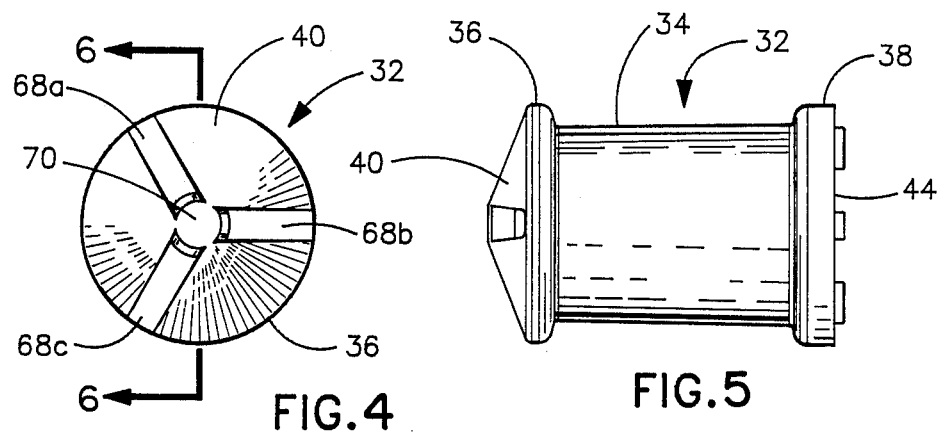
FIG. 4
FIG. 5
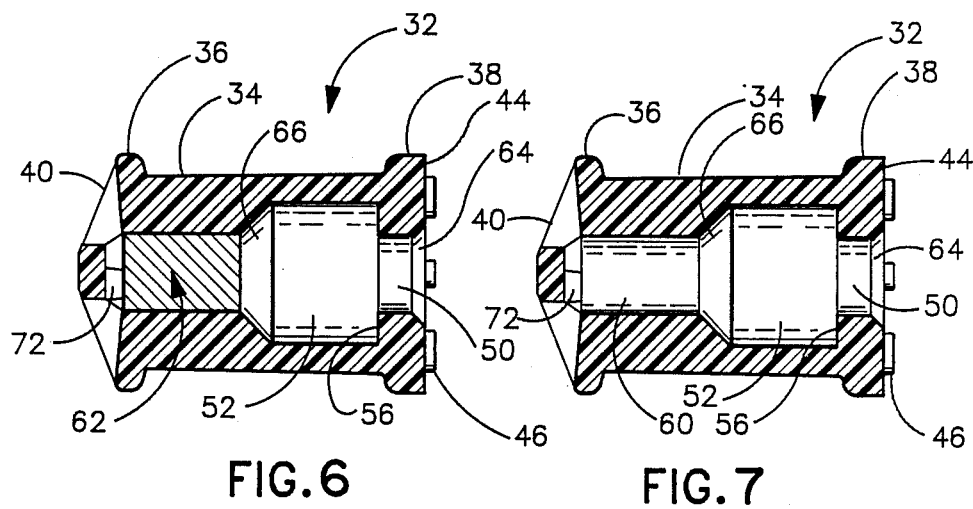
FIG. 6
FIG. 7
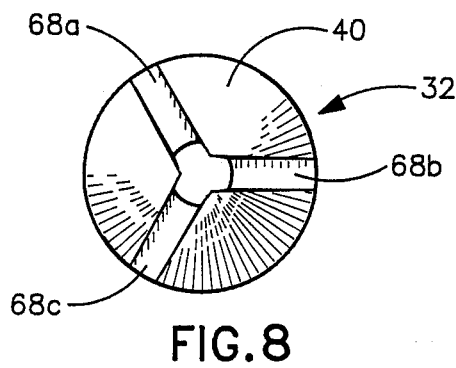
FIG. 8

ARTERIAL BLOOD GAS SYRINGE

FIELD OF THE INVENTION

The present invention relates to syringes and, in particular, arterial blood gas syringes.

BACKGROUND INFORMATION

An arterial blood gas syringe is used in obtaining an arterial blood sample from a patient. The arterial blood sample is then inputted or transferred to a blood gas analyzer to analyze the gas components of the blood sample. The concentration of known gas components in the blood sample is useful in diagnosing the condition of the patient.

A number of differently configured arterial blood gas samples have been advanced or devised for drawing the arterial blood sample from the patient. Current commercially available arterial blood gas syringes include elements commonly found in syringes, namely, a syringe barrel, a sealing plug and a plunger rod. The sealing plug is connected to the tip of the plunger rod and is used in defining a blood receiving space within the syringe barrel. Such syringes are also characterized by the use of filter media connected to the sealing plug or plunger rod. Generally, the filter acts to permit air to pass from the blood receiving space while preventing the flow of blood past the sealing plug. The differences among the various prior art syringes lie primarily in the design or construction of the sealing plug, although there are syringes that differ in plunger rod construction. In connection with devising an arterial blood gas syringe including a filter, it is desirable to achieve a relatively rapid fill time of the blood receiving space, while avoiding or minimizing the time associated with the unwanted diffusion of gas into the obtained blood sample. Such gas diffusion primarily occurs through the filter, although there is some diffusion past the wall of the syringe barrel. In achieving these important objectives, it is also important to provide an arterial blood gas syringe that can be made with few, and relatively inexpensive parts, while the assembly time associated therewith is minimized and the cost of assembly is also reduced. Although known prior art arterial blood gas syringes function satisfactorily for their intended purpose, it still remains desirable to provide an arterial blood gas syring that improves on the desired furnctions associated with such a syringe while keeping the cost of such a syringe to a minimum.

An arterial blood gas syring is disclosed in U.S. Pat. No. 4,424,817 to Williams, issued Jan. 10, 1984, entitled "Syringe With Means For Automatically Sealing A Blood Sample Within The Syringe" and assigned to same assignee as is the present invention. This syringe includes a sealing plug having a number of longitudinal channels formed about the circumference thereof. In communication with each of the longitudinal channels is a lateral channel that communicates with the interior of the sealing plug. Because of the higher pressure required to move blood along the relatively small area of the channels, as well as the fact that the surface of the blood is not easily broken because of the conical-shaped tip of the sealing plug, the blood will tend to fill the blood receiving space before it moves along the channels to any great extent. The plunger rod of this syringe has a cavity for receiving an elongated, cylindrical-shaped filter. The plunger rod is hollow for use in providing an air passageway to the outside environment from the filter. In cases in which it is desirable to aspirate blood into the syringe, the open end of the hollow plunger rod is closed off by the thumb or finger of the syringe user to prevent communication between the atmosphere and the inside of the hollow plunger rod. The plunger rod is then withdrawn creating a vacuum in the blooc receiving space so that the arterial blood is drawn therein.

U.S. Pat. No. 4,466,446 to Baidway, et al., issued Aug. 21, 1984, entitled "Plunger Assembly For Blood Gas Syringes" and assigned to the same assignee as is the present invention discloses an arterial blood gas syringe characterized by a particular construction for achieving aspiration. It is presently common practice to preset the sealing plug and plunger rod at a desired or predetermined position in the syringe barrel to define the blood receiving space. If, when taking a blood sample, the patient's arterial blood pressure is insufficient to cause a complete filling of the defined blood receiving space then aspiration can be achieved by retracting the plunger rod. By pulling back on the plunger rod the opposing surfaces of the sealing plug and plunger rod contact each other thereby forming a seal which terminates the air pathway between the outside atmosphere and the blood receiving space. Further retraction of the plunger rod produces lower pressure in the blood receiving space which causes the arterial blood to be drawn therein. This syringe also includes a filter for use in permitting the passage of air while stopping the flow of blood. This filter is located within the interior of the sealing plug and is measurably spaced from the upper surface of the sealing plug. The sealing plug of the syringe also has longitudinally-extending grooves formed about the circumferential periphery thereof. These grooves communicate with laterally-extending passageways, which communicate with the interior of the sealing plug.

In addition to the foregoing known blood gas syringes, representative of commercially available syringes, are the Bard-Parker ABG Mini-Kit syringe package and the PREZA-PAK II sampler syringe of Terumo Corporation. The Bard-Parker syring is characterized by a filter that is joined to an outer surface of a sealing plug and extends outwardly into the blood receiving space from the sealing plug. The filter is disc-shaped and has a diameter substantially corresponding to the inside diameter of the syringe barrel. The filter also has a stem section, which is integral with the disc-shaped section. The stem is received in a hole formed in the sealing plug to connect the filter to the sealing plug. The Terumo arterial blood gas syringe includes a sealing plug having a recessed cavity communicating with the blood receiving space and defined by a circumferential wall of the sealing plug. The circumferential wall fans outwardly in a direction towards the blood receiving space whereby the thickness of the wall decreases in a direction towards the blood receiving space. A filter is located within the recessed cavity, with the upper surface thereof completely exposed to the blood receiving space and spaced from the upper edge of the sealing plug. Like the syringe disclosed in U.S. Pat. No. 4,424,817, this syringe includes a hollow plunger rod in which aspiration can be achieved by preventing communication between the outside environment and the filter by closing off the plunger rod passageway.

SUMMARY OF THE INVENTION

The objectives of the present invention include providing an arterial blood gas syringe that has a rapid fill time to minimize the time taken to obtain the blood sample, that is able to purge air frm a blood receiving space to avoid contamination of the blood sample, that requires few parts, that reduces syringe assembly time, and that can be manufactured at low cost.

The arterial blood gas syringe of the present invention includes a barrel with an open end and a tapered end, a plunger rod with an attachment rip, a sealing plug containing a filter element, and a hypodermic needle.

The barrel, plunger rod, and the hypodermic needle are all of the kind conventionally employed in the art. The barrel is typically of circular cross section, made of plastic or glass, has an open end to receive the plunger rod and sealing plug, and has a tapered end to which the hypodermic needle is connected. The plunger rod has a platform for use in moving the plunger rod, a shaft which makes up most of the length of the plunger rod, and a tip which is used to attach the plunger rod to the sealing plug. The hypodermic needle is of a kind typically used with variously configured syringes.

Of primary interest in achieving the objectives of the present invention is the sealing plug. The sealing plug is attached to the plunger rod which, in turn, fits within the open end of the barrel. The plunger rod is then used to position the sealing plug in the barrel. The position of the sealing plug relative to the tapered end of the barrel defines a blood receiving space. As the name implies the sealing plug confines the blood sample to the blood receiving space. This is accomplished in part by the filter element which allows air to escape from the defined space but not the obtained blood sample. This feature enables the operator of the syringe to rapidly obtain a blood sample while reducing air contamination. Consequently, an accurate blood gas analysis can be subsequently conducted using the blood sample.

The objectives of low cost, relatively simple construction, and ease of assembly are achieved through the design of the sealing plug. The essential portions of the plug are upper and lower surfaces, a main body, a hollow interior section, and channels formed in the upper surface, which communicate with the hollow interior section.

The upper and lower surfaces which form the ends of the sealing plug are of a greater radii than the main body and the inside radius of the barrel. This configuration defines two sealing rims which provide the airtight seal that confines the blood sample to the blood receiving space. In addition, the use of two sealing rims serves to stabilize the sealing plug in the barrel of the syringe.

The inner, hollow section of the sealing plug houses the filter and provides a pathway for air to exit the blood receiving space as the space is being filled with blood. The lower part of the hollow section acts as a connector for the plunger rod tip.

The conically shaped upper surface in cooperation with the channels that are radially disposed in the upper surface serve to bias contaminating air in the blood receiving space toward the filter element while tending to discourage blood from reaching the filter element. Consequently, by the time blood reaches the filter element the air is purged from the blood receiving space.

Because of the uniquely configured sealing plug, the major objectives of producing a relatively inexpensive syringe while achieving rapid fill time and reducing unwanted air diffusion are met.

BRIEF DESCRIPTION OF THE DRAWINGS

FIG. 1 is an exploded perspective view of the arterial blood gas syringe of the present invention;

FIG. 2 is a perspective view illustrating the engagement of the syringe parts and the defining of a blood receiving space;

FIG. 3 is an enlarged perspective view of the sealing plug with portions thereof cutaway;

FIG. 4 is an end view of the upper surface of the sealing plug;

FIG. 5 is a side view of the sealing plug;

FIG. 6 is a cross sectional side view of the sealing plug with a filter in the filter receiving section taken across line 6—6 of FIG. 4;

FIG. 7 is a cross sectional side view of the sealing plug without a filter in the filter receiving section taken across line 6—6 of FIG. 4;

FIG. 8 is an end view of the upper surface of the sealing plug of another embodiment in which a center plug element is removed.

DESCRIPTION OF THE PREFERRED EMBODIMENTS

In accordance with the present invention, an arterial blood gas syringe 10 is disclosed for obtaining an arterial blood sample from a patient. With reference to FIG. 1, the arterial blood gas syringe 10 includes a syringe barrel 12 for receiving and containing an arterial blood sample. The syringe barrel 12 is a conventional unit of a desired size and can be made of a suitable material, such as glass or plastic. The syringe barrel 12 has a chamber 14 defined by the inner cylindrical wall of the barrel 12. The barrel 12 also has a platform end 16, which is commonly used by the user or operator in grasping the barrel 12 and using the syring 10 in obtaining the arterial blood sample. The opposite end of the syringe barrel 12 has a conventional luer tip 18 for receiving a standard syringe needle 20 and for connecting the needle 20 to the syringe barrel 12.

The syringe 10 also includes a plunger rod 22, which is positionable and movable within the syringe barrel 12 and is used in defining a predetermined volume of arterial blood to be taken from a patient for subsequent analysis. The plunger rod 22 is also a conventional unit and has an enlarged end 24, which is grasped by the user in adjusting the plunger rod relative to the chamber 14 of the syringe barrel 12. A shaft 26 is integrally joined to the enlarged end 24 and terminates at a disk-shaped end 28. Extending from the disk-shaped end 28 is a plunger rod tip or head 30. The head 30 is used in attaching the plunger rod 22 to a sealing plug 32.

The sealing plug 32 of the present invention has a novel configuration and reference is now made to FIGS. 3–7 to describe this construction. The sealing plug 32 is a one-piece article and is fabricated from rubber or another synthetic elastic material that is substantially impervious to gases, particularly oxygen and carbon dioxide, the concentrations of which two gases must be accurately determined during the blood gas analysis using the arterial blood sample. The sealing plug 32 includes a cylindrical body 34 that terminates at opposite ends with first and second sealing rims 36, 38. The first sealing rim 36 is located adjacent to an upper surface or face 40 of the sealing plug 32 while the opposite end of the body 34 is adjacent to the second sealing rim 38. The second sealing rim 38 is located adjacent to a lower surface 44 of the sealing plug 32. Each of the two sealing rims 36, 38 is used in providing a seal and preventing blood flow past the sealing plug 30, just as is the case in other well-known syringe plugs. The lower surface 44 of th sealing plug 30 has a number of spacers 46 that extend outwardly. The spacers 46 are used in maintaining an air passageway to the outside environment or atmosphere when using the syringe 10.

With particular reference to FIGS. 6 and 7, a number of hollow sections are seen to be formed in the sealing plug 32. Specifically, an outer hollow section 50 is formed in the mid portion of the second sealing rim 38 and the outer hollow section 50 communicates with an intermediate hollow section 52. The hollow section 52 has a greater diameter than that of the hollow section 50 whereby a ledge 56 is formed in the body 34 of the sealing plug 32. the diameter of the intermediate hollow section 52 is greater than the width or diameter of the plunger head 30 wherein the bottom surface of the plunger head 30 is able to rest on and engage the ledge 56 for use in positioning the sealing plug 32 and creating a seal if it is necessary to aspirate the blood sample, i.e., an air passageway between the inside of the sealing plug 32 and the outside atmosphere is closed or shut off. Relatedly, the diameter of the outer hollow section 50 is somewhat smaller in diameter than the width of the plunger head 30 so that some degree of force must be exerted on the plunger rod 22 in order to position the head 30 in the intermediate hollow section 52 past the outer hollow section 50. In addition to the hollow sections 50, 52, the sealing plug 32 also has an inner hollow section 60, which communicates with the intermediate hollow section 52 and extends to the upper surface 40 of the sealing plug 32.

As seen in FIGS. 3 and 6, the syringe 10 also includes a filter element 62 which is located and held in the inner hollow section 60. The filter element 62 is preferably cylindrical-shaped, having a length greater than its diameter, and occupies the space defined by the inner hollow section 60. In order to insure that blood does not escape past the filter element 62, a tight, sealing-like fit is produced by making the diameter of the inner hollow section 60 slightly smaller than the diameter of the filter element 62. Since the sealing plug 32 is made of an elastic material, the inner hollow section 60 is expandable to accommodate the insertion of the filter element 62. After insertion, the elastic nature of the sealing plug 32 holds the filter element 62 securely in place. In one preferred embodiment, the filter element 62 is a hydrophobic filter that permits the passage of air or gas but prevents the passage of a liquid, such as blood. Such filters are now commonly used in arterial blood gas syringes.

Also formed in the sealing plug 32 are first and second beveled hollow sections 64, 66. The first beveled section 64 is located at the lower surface 44 and the second beveled section 66 is located between the inner and intermediate hollow sections 52, 60. Beveled sections 64, 66 facilitate the insertion of filter element 62 into inner hollow section 60. Additionally, beveled section 64 promotes the insertion and receipt of the plunger rod head 30 into the sealing plug 32.

With particular reference to FIG. 4, the upper surface 40 of th sealing plug 32 is formed with a plurality of channels 68a, 68b, 68c. Although three channels 68 are illustrated, a different number of channels could be utilized. Preferably, each of the channels 68a-68c starts at the edge of the first sealing rim 36 and extends towards the center of the upper surface 40 of the sealing plug 32. The width of each of the channels 68a-68c is such that a pressure differential is created which causes blood to fill a desired space in the syringe barrel chamber 14 before any blood enters the channels 68a-68c. In particular, each of the channels 68a-68c has a slightly greater width near the center of the upper surface 40 than at the first sealing rim 36. As can also be seen in FIGS. 6-7, the upper surface 40 is conically shaped to assist in causing the air in the space to be occupied by the blood to move towards the edge or periphery of the upper surface 40 so that the air is carried by the channels 68a-68c towards the filter element 62. The depth of each of the channels 68a-68c increases with the distance away from the edge of the first sealing rim 36 so that air is forced in a direction towards the filter element 62. In the embodiment of FIG. 4, at the center of the radially-extending channels 68a-68c, a center plug element 70 remains or is formed at the center of the upper surface 40. This is, each of the channels 68a-68c terminates at the cente rplug element 70. Additionally, a gap 72 is provided beneath the center plug element 70. The gap 72 constitutes a further space that must be traversed by an air that might be diffusing back through the filter element 62 for entry into the obtained blood sample, before the blood has been removed for analysis.

Near the center plug element 70 in the upper surface 40, in one embodiment, when the sealing plug 32 is made by injection molding or the like, an opening or slit is formed whereby there is communication between each of the channels 68a-68c and the filter element 62. Consequently, when fluid does pass along one or more of the channels 68a-68c, it is able to pass to and contact the filter element 62. With regard to effecting communication between the channels 68a-68c and the filter element 62, "flash" might result during molding of the sealing plug 32. That is, instead of the desired communication, a very thin layer of sealing plug material could be interposed between the filter element 62 and the channels 68a-68c. In such a case, any such thin layer or membrane can be pierced by conventional means to create the necessary communication.

In another embodiment of the sealing plug 32, with reference to FIG. 8, the upper surface 40 is made or formed without the center plug element 70. In this embodiment, the top of the filter element 62 is entirely exposed whereby fluid in the channels 68a-68c is able to pass to the filter element 62 without necessarily flowing through an opening or slit in the bottom of the channels 68a-68c.

With regard to production and assembly of the sealing plug 32 and the filter element 62, the sealing plug 32 is preferably made using a one step molding tool. For each sealing plug 32 manufactured, a filter element 62 is inserted into the inner hollow section 60 of the sealing plug 32. This can be accomplished by relatively simple and inexpensive tooling due to the linear communication among the hollow sections 50, 52, 60. In one embodiment, the filter element 62 is placed in a sleeve of a tool which is guided the by first and second beveled sections 64, 66 into the inner hollow or filter receiving section 60. The filter element 62 is then deposited in the inner hollow section 60 by having a rod within the sleeve hold the filter element 62 in place while the sleeve is withdrawn.

When using the arterial blood gas syringe 10 of the present invention, the plunger rod 22 and the sealing plug 32 connected thereto are positioned within the chamber 14 of the syringe barrel 12 at a desired or predetermined position to define a blood receiving space 74, as seen in FIG. 2. The blood receiving space 74 corresponds to the volume of the arterial blood sample to be obtained from a patient. The space 74 is defined by the operator moving the plunger rod 22 and the sealing plug 32 along the longitudinal extent of the chamber 14. After the blood receiving space 74 is defined, the user accesses an artery using the needle 20. The patient's arterial blood pressure forces the blood through the needle 20 and into the blood receiving space 74. As previously described, the conical shape of the upper surface 40 and the channels 68a–68c cooperate to bias air toward the filter element 62 and discourage the flow of blood toward the filter element 62. The filter element 62 allows contaminating air to pass therethrough and into and through the hollow sections 52, 50 whereby such air passes to the outside environment. The spacers 46 provided on the lower surface 44 of the sealing plug 32 insure that the plunger rod head 28 does not block the flow of the air to the outside environment. The contaminating air is thereby purged from the blood receiving space 74 and passes through the filter element 62 before blood enters the channels 68a–68c. Consequently, by the time blood reaches the filter element 62, the blood receiving space 74 has been purged of air and contains an arterial blood sample that is ready for inputting to the blood gas analyzer.

Based on the foregoing detailed description, a number of worthwhile benefits of the present invention are immediately recognized. An arterial blood gas syringe is provided for obtainin g an arterial blood sample in a relatively rapid manner while purging air from the blood receiving space. The sealing plug is uniquely configured to house a filter element for permitting air to pass but not blood and includes radially-extending channels for use in removing the air from the blood receiving space. The sealing plug can be inexpensively manufactured and then assembled with the filter element. The combination of the sealing plug and the filter element are also constructed to reduce diffusion of air back therethrough into the blood sample after it has been obtained from the patient and prior to insertion of the blood sample into the blod gas analyzer.

While the apparatus herein described constitutes the preferred embodiment of the invention, it is understood that the invention is not limited to this exact apparatus and that changes can be made without departing from the scope of the invention, which is defined in the appended claims.

What is claimed is:
1. A syringe, comprising:
a syringe barrel including a tapered end and an open and and having an inner wall surface;
a plunger rod having a tip;
a sealing plug connected to said plunger rod tip for preventing the flow of blood past said open end of said syringe barrel, said sealing plug having an upper surface and a hollow interior with an inner hollow section being defined in said hollow interior, said upper surface of said sealing plug having a plurality of channels extending laterally across said upper surface, said channels being of a size wherein blood tends to fill a blood receiving space defined between said upper surface and said tapered end of said syringe barrel before the blood moves along said channels; and
filter means held in said inner hollow section for use in permitting the passage of air from said blood receiving space while preventing the passage of blood from said blood receiving space, said channels providing a passageway for air from said blood receiving space to said filter means.
2. A syringe, as claimed in claim 1, wherein:
said upper surface of said sealing plug includes an sealing rim positioned adjacent to said inner wall surface of said syringe barrel to contain blood in said blood receiving space.
3. A syringe, as claimed in claim 2, wherein:
one end of each of said channels is located at said sealing rim for use in ensuring that no unwanted, trapped air remains in said blood receiving space.
4. A syringe, as claimed in claim 2, wherein:
said upper surface of said sealing plug is conically shaped for biasing air to said channels.
5. A syringe, as claimed in claim 2, wherein:
each of said channels extends substantially radially from said annular ring of said sealing plug towards a center portion of said upper surface of said sealing plug.
6. A syringe, as claimed in claim 5, wherein:
the width of at least one of said channels is greater adjacent said center portion of said sealing plug than said width thereof adjacent said sealing rim of said sealing plug.
7. A syringe, as claimed in claim 2, wherein:
each of said channels has a lower surface with a slope to insure that no unwanted, trapped air remains in said channels.
8. A syringe, as claimed in claim 1, wherein:
said upper surface of said sealing plug has a center plug element at which each of said channels terminates, said center plug element being located substantially at a midportion of said filter means.
9. a syringe, as claimed in claim 1, wherein:
the length of said inner hollow section is greater than the diameter of said inner hollow section.
10. A syringe, as claimed in claim 1, wherein:
said filter means is generally cylindrical-shaped having a length greater than the diameter thereof.

* * * * *